United States Patent [19]

Gleason et al.

[11] 4,103,086

[45] Jul. 25, 1978

[54] 8-OXO-4-THIA-1-AZABICYCLO (4.2.0)-OCT-2-ENE DERIVATIVES

[75] Inventors: John G. Gleason, Delran; Kenneth G. Holden, Haddonfield, both of N.J.; William F. Huffman, Malvern, Pa.

[73] Assignee: SmithKline Corporation, Philadelphia, Pa.

[21] Appl. No.: 693,992

[22] Filed: Jun. 8, 1976

Related U.S. Application Data

[63] Continuation-in-part of Ser. No. 626,686, Oct. 29, 1975, abandoned, which is a continuation-in-part of Ser. No. 574,225, May 5, 1975, abandoned.

[51] Int. Cl.$^2$ ............................................. C07D 279/08
[52] U.S. Cl. ....................................... 544/47; 424/246
[58] Field of Search ....................... 260/243 R; 544/47

[56] References Cited

PUBLICATIONS

Cephalosporins and Penicillins, (Editor) Edwin H. Flynn, Academic Press, New York, (1972) p. 80.
Protective Groups in Organic Chemistry, (Ed.) J. F. W. McOmie, Plenum Press, New York, (1973) pp. 43–93 and pp. 183–215.

Primary Examiner—John M. Ford
Attorney, Agent, or Firm—Stuart R. Suter; Alan D. Lourie; William H. Edgerton

[57] ABSTRACT

Novel bicyclic β-lactams and intermediates useful in their preparation are disclosed. In particular, 7β-acylamino- and 7β-amino-8-oxo-4-thia-1-azabicyclo[4.2.0]oct-2-ene-2-carboxylic acids are prepared. The acylated compounds are antibacterial agents.

58 Claims, No Drawings

8-OXO-4-THIA-1-AZABICYCLO (4.2.0)-OCT-2-ENE DERIVATIVES

This application is a continuation-in-part of copending application Ser. No. 626,686 filed Oct. 29, 1975 which is a continuation-in-part of Ser. No. 574,225 filed May 5, 1975, both now abandoned.

This invention relates to cephalosporin-like compounds which have antibacterial activity and to chemical compounds and methods useful to prepare these novel antibacterial agents.

BACKGROUND

Cephalosporins obtained by fermentation processes or ring expansion of penicillins all contain the 8-oxo-5-thia-1-azabicyclo[4.2.0]oct-2-ene nucleus, i.e.

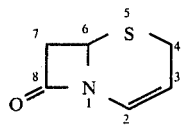

Compounds with this ring system have been the object of intense research and numerous scientific articles and patents. As a result of this effect, approximately eight commercial products are available today as antibacterial agents.

Analogous rings systems in which the sulfur atom has been moved to another position in the six-membered ring can not be obtained by the same methods as described for the above nucleus. A totally synthetic approach to this ring system must be employed. One system which has been attempted with varied success is the 8-oxo-4-thia-1-aziabicyclo[4.2.0]octane for which the trivial name isocephalosporin can be given, i.e.

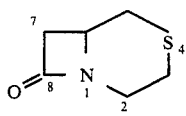

The synthesis of 7$\beta$-phenylacetamido-7$\alpha$-methyl-6$\alpha$H-8-oxo-4-thia-1-azabicyclo[4.2.0]oct-2-ene-2-carboxylic acid and the 2,3-dihydro derivative has been reported in *J. Chem. Soc.* 1321 (1973). These compounds lack the 2-3 double bond believed necessary for biological activity and/or have a 7$\alpha$-methyl group which is not present in naturally occurring cephalosporins. These two compounds were reported to have no antibacterial activity when tested at high levels against three bacteria. Also reported within this reference was a derivative with transconfiguration, 7$\alpha$-phenylacetamido-6$\alpha$H-8-oxo-4-thia-1-aza[4.2.0]octane-2-carboxylic acid. This compound also showed no activity. Within this reference attempts to prepare the nucleus without the methyl substituent and with the 2-3 double bond were unsuccessful. Further attempts were reported in *J. Chem. Soc. Perkin I,* 2092 (1974) and were also unsuccessful.

We have now prepared the 6,7$\alpha$H-8-oxo-4-thia-1-azabicyclo[4.2.0]oct-2-ene ring system; in particular, 7$\beta$-acylamino-6$\alpha$H-8-oxo-4-thia-1-azabicyclo[4.2.0]oct-2-ene-2-carboxylic acids and derivatives thereof.

SUMMARY OF THE INVENTION

The compounds of this invention are represented by the following structural formula:

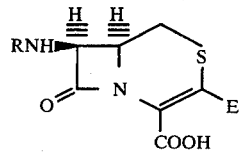

Formula I wherein
R is an acyl group and
E is hydrogen, methyl, bromomethyl, or lower alkanoyloxymethyl.

The term acyl group refers to any acyl group used within the cephalosporin and penicillin art, except phenylacetyl. Preferred acyl groups are represented by the general formulae:

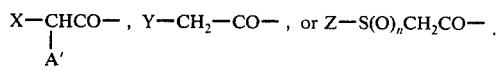

Especially preferred acyl groups are those where X is thienyl, cyclohexyl, cyclohexenyl, cyclohexadienyl, phenyl, or phenyl substituted with one or two substituents selected from the group consisting of lower alkyl, lower alkoxyl, hydroxy, hydroxymethyl, halo, nitro, amino, aminomethyl, mercapto, lower alkylthio, trifluoromethyl, ureido, formamido, and carboxymethylamino; A' is amino, hydroxy, formyloxy, carboxyl, or sulfonic acid; Y is cyano, azido, phenoxy or a 5 or 6-membered heterocyclic ring containing 1-4 heteroatoms selected from the group consisting of nitrogen, oxygen and sulfur; Z is phenyl, pyridyl, lower alkyl, trifluoromethyl, trifluoroethyl, or cyanomethyl and n is 0, 1 or 2. The 5 or 6-membered heterocycles include thienyl, furyl, thiazoyl, isothiazolyl, oxadiazolyl, thiadiazolyl, triazolyl, tetrazolyl, sydnone, pyridyl, pyrimidyl and the like. The heterocyclic group may be unsubstituted or substituted with substituents selected from lower alkyl, halo, hydroxy, nitro, amino, lower alkoxy, aryl such as phenyl, lower aralkyl and the like.

The terms lower alkyl, lower alkoxy and lower aralkyl used within this entire disclosure refers to alkyl groups containing one to six carbon atoms. The term halogen or halo includes fluorine, chlorine and bromine.

The compounds which are also a part of this invention and which are useful as intermediates to prepare compounds of Formula I are represented by Formula II:

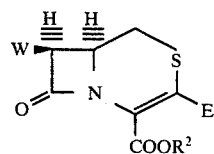

Formula II wherein
E is hydrogen, methyl, bromomethyl or lower alkanoyloxymethyl;
W is R'$_2$N;
R$^2$ is hydrogen or removable carboxyl protecting group; and each R' is hydrogen or a monovalent removable amine protecting group or when both R' groups are taken together, a divalent amine protecting group.

Lower alkanoyloxymethyl in both Formulae I and II refers to alkanoyl groups of one to six carbon atoms. A preferred member within this group is acetoxymethyl.

Another group of compounds which are a part of this invention and are useful intermediates for the preparation of the compounds of Formulae I and II are represented by Formula III:

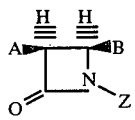

Formula III wherein
A is $N_3$, $NH_2$, acylamino, or protected amino;
B is COOY or $CH_2X'$;
Y is hydrogen or lower alkyl;
X' is OM, halogen, p-methoxybenzylthio, triphenylthio, or mercapto;
M is hydrogen, lower alkylsulfonyl or phenylsulfonyl, said phenyl being unsubstituted or substituted with methyl or halogen; and
Z is hydrogen or 2,4-dimethoxybenzyl.

The term "removable carboxyl protecting group" is a term which has acquired a definite meaning within the cephalosporin and organic chemical arts. Many groups, particularly many ester groups, are known which are used to protect the carboxyl groups during subsequent chemical reactions and later removed by standard methods to give the free carboxylic acid group. Known ester protecting groups include 2,2,2-trichloroethyl, $C_4$-$C_6$-tert-alkyl, such as t-butyl, $C_5$-$C_7$-tert-alkenyl, $C_5$-$C_7$-tert-alkynyl, $C_1$-$C_6$-alkanoylmethyl, N-phthalimidomethyl, benzoylmethyl, halobenzoylmethyl, methylbenzoylmethyl, methanesulfonylbenzoylmethyl, phenylbenzoylmethyl, benzyl, nitrobenzyl, methoxybenzyl, benzhydryl, trityl, trimethylsilyl, triethylsilyl and the like. The choice of which ester group to use is well within the ability of one skilled in the art. Factors which are considered include what subsequent reaction conditions the group must withstand and what conditions for removing the protecting ester is desirable. Groups which are removed by treatment with trifluoroacetic acid, hydrogenation or zinc dust and acetic acid have been preferred in the art when a β-lactam is fused to a six-member ring. The choice of the protecting group is not critical to our invention since the novelty of our invention lies within the new bicyclic nuclei and not the ester substituents.

A "removable amine protecting group" or a "protected amino group" are terms well known in the art. They refer to amino groups which have been masked by another group so as to protect them during subsequent chemical reactions and then the masking group can be removed to generate again the desired amino moiety. Many groups are known and used for this purpose within the penicillin, cephalosporin, and peptide synthetic arts. Examples of these include, t-butoxycarbonyl, trichloroethoxycarbonyl, benzyloxycarbonyl, p-methoxybenzylcarbonyl, isobornyloxycarbonyl, trityl, methyl acetoacetate adduct and the like which are monovalent protecting groups. Divalent protecting groups include phthaloyl and the 4,5-diphenyl-4-oxazolin-2-one group. Treatment of a phthalimido group with hydrazine by published procedures cleaves the phthaloyl group to regenerate the amino group. Preparation and removal of the 4-oxazolin-2-one group is taught in the art; *J. Org. Chem.*, 38, 3034 (1973). The choice of the protecting group depends on various factors including the subsequent chemical reaction conditions and the desired conditions for removal of the protecting group. However, this choice is within the ordinary ability of one skilled in the art. Again the choice of the amino protecting group is not critical to our invention for the same reasons given above about the carboxyl protecting group.

The term acyl group means any acyl group which has been used in the semisynthetic penicillin and cephalosporin fields except phenylacetyl including the following examples:

α-hydroxyphenylacetyl
α-formyloxyphenylacetyl
α-aminophenylacetyl
α-amino-4-hydroxyphenylacetyl
α-amino-4-hydroxy-3-fluorophenylacetyl
α-amino-4-carboxymethylaminophenylacetyl
trifluoromethylmercaptoacetyl
methylmercaptoacetyl
methylsulfonylacetyl
2,2,2-trifluoroethylsulfinylacetyl
cyanoacetyl
cyanomethylmercaptoacetyl
cyanomethylsulfinylacetyl
cyanomethylsulfonylacetyl
α-carboxy-2-thienylacetyl
α-carboxy-3-thienylacetyl
α-carboxyphenylacetyl
α-sulphophenylacetyl
3-sydnoneacetyl
2-thienylacetyl
3-thienylacetyl
1-tetrazolylacetyl.

SCHEME I

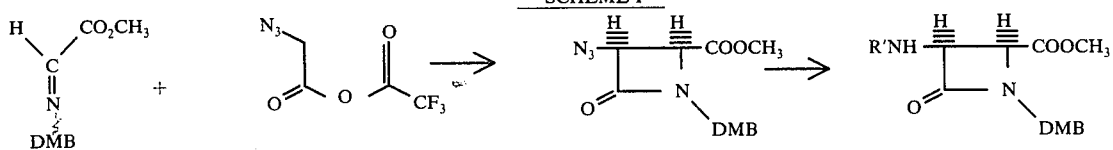

DMB = 2,4-dimethoxybenzyl 1     2     3     4
↓

-continued
SCHEME I

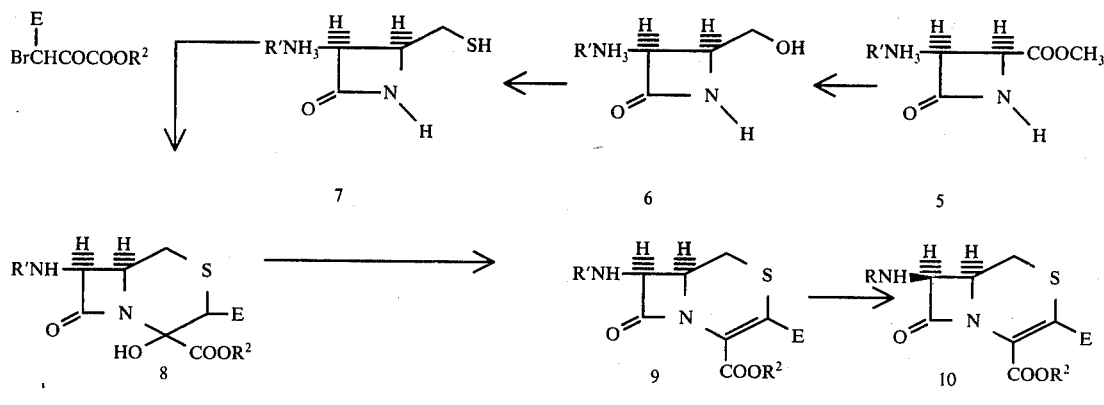

The compounds of this invention set forth in Formulae I and II contain a nucleus which is related to naturally occuring cephalosporins but which cannot be prepared by fermentation methods. Therefore, the compounds are prepared by a totally synthetic route as outlined in Scheme I. Within Scheme I, R is any acyl group as set out above or a derivative thereof in which any chemically sensitive group such as carboxy, hydroxy or amino is protected with a standard removable protecting group, many of which have been described above, until the final step of the reaction sequence. Many protective groups are set forth in the book "Protective Groups in Organic Chemistry", ed. J. F. W. McOmie, Plenum Press, New York, 1973 and in other review articles and books. R' is an amino protecting group which is removed after the 4-thia-1-azabicyclo[4.2.0]-oct-2-ene nucleus is formed to give the 7-amino derivative. This derivative can then by acylated by the same standard methods used within the cephalosporin art with the desired acyl group to give the compounds of this invention. $R^2$ is a protective ester residue used to protect the carboxyl group and is also removable at the end of the reaction sequence to give the final active products which contain a free carboxyl group or a salt thereof.

The important intermediate which gives the new nucleus its 6,7-cis configuration is methyl cis-1-(2,4-dimethoxybenzyl)-3-azido-4-oxoazetidine-2-carboxylate (3). This compound is prepared by the cyclo addition reaction between the imine obtained from the condensation of 2,4-dimethoxybenzylamine and methyl glyoxalate and a mixed anhydride or acid halide of azidoacetic acid. The azido group of this intermediate is reduced by catalytic hydrogenation or by chemical reduction such as zinc and acetic acid to give the 3-aminoazetidine derivative. The amino group can be protected by a removable amino protecting group such as t-butoxycarbonyl. A protected 3-aminoazetidine derivative can also be prepared directly by substitution of a glycine derivative in which the amino group has been protected. For example, 4,5-diphenyl-2-oxo-4-oxazolin-3-ylacetic acid or N-phthalimidoacetic acid can be used in the cyclization reaction in the same manner as azidoacetic acid to give the corresponding protected 3-aminoazetidine derivative.

The intermediate 3 or a protected 3-aminoazetidine described above can be converted by a series of reactions into the 2-methylsulfonate derivatives as illustrated by compound 11 in Scheme II. Varied reaction sequences can be used in the preparation of compounds like 11. Scheme II sets forth two alternate pathways which can be used to go from compound 3 to compound 11. It is apparent to persons skilled in the art that conversion of the azido group to the protected amino is not limited to the two illustrated places along the reaction sequence but can also be done at other alternative places. Reduction of the azido moiety is advantageously done on compound 3 in Scheme II or on the 3-azido-2-methyl tosylate derivative 12.

The methylsulfonate derivatives (11) is then converted stepwise to the mercaptomethyl derivative 7 as set forth in Scheme III. The sulfonate is displaced with iodide ion which is in turn displaced with a mercaptan derivative such as p-methoxybenzyl mercaptan or triphenylmethyl mercaptan. Cleavage of these derivatives by standard synthetic methods gives the mercaptomethyl compound 7. The p-methoxybenzyl group is cleaved by treatment with mercuric salts. The triphenylmethyl group is cleaved by treatment with silver salts including silver nitrate and silver tetrafluoroborate and therefore is advantageous if other groups within the compound is sensitive to mercuric ion.

SCHEME II

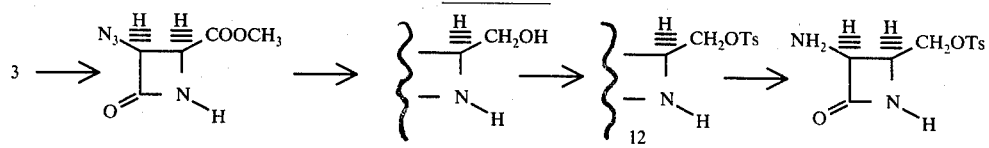

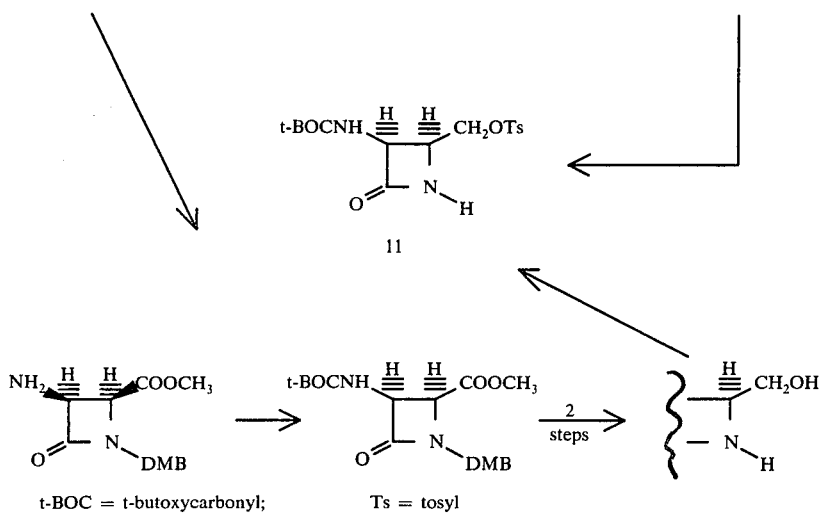

t-BOC = t-butoxycarbonyl; Ts = tosyl

SCHEME III

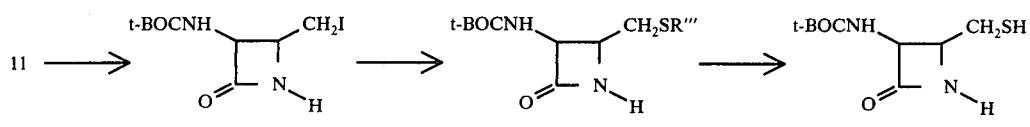

R''' = p-methoxybenzyl or triphenylmethyl

The mercaptomethyl compound 7 is reacted with a β-bromo-α-keto ester to give the bicyclic system as shown in compound 8. When a bromopyruvate ester is used, compound 8 where E is hydrogen is obtained. When a 3-bromo-2-ketobutyrate ester is used, compound 8 where E is methyl is obtained. These compounds are dehydrated to give the 8-oxo-4-thia-1-azabicyclo[4.2.0]oct-2-ene system 9. Standard dehydration reagents such as thionyl chloride, trifluoroacetic anhydride, and methanesulfonyl anhydride are used.

Compounds of structure 9 where E is bromomethyl are prepared by radical bromination of the 3-methyl compounds using the procedures known in the cephalosporin art. Bromination reagents include N-bromosuccinimide in the presence of radical initiators such as benzoyl peroxide or azobisisobutyronitrile.

The bromomethyl derivatives can be reacted with various acetate salts to give compounds of structure 9 where E is acetoxymethyl. Exemplary salts useful for this purpose include sodium, potassium, or silver acetate.

Compounds of structure 10, the antibacterial agents of this invention, are prepared from compounds of structure 9 by removal of the amino protecting group followed by acylation with the desired acyl group using standard acylation methods. Following the acylation any additional protecting groups are removed. During the acylation reaction any sensitive groups such as amino or hydroxy are protected as has been previously described. Standard acylation methods include activation of the carboxyl by use of mixed anhydrides, activated esters, and acid halides or by use of coupling reagents such as dicyclohexylcarbodiimide.

Some compounds within the scope of Formula I can alternatively be prepared by acylation with the desired acyl group earlier in the reaction sequence. For example, the 3-aminoazetidone derivative can be prepared and acylation at the same places as those disclosed in Scheme II. When this acylated monocyclic β-lactam is carried along the reaction sequence herein disclosed the desired final products are obtained. Examples of acyl groups for which this alternate method can be used include phenoxyacetyl, α-aminophenylacetyl, α-amino-p-hydroxyphenylacetyl, 2-thienylacetyl and the like.

More specifically, when 2,4-dimethoxybenzylamine [Chem. Ber., 101, 3623 (1968)] is condensed with methyl glyoxalate [Synthesis, 544 (1972)], imine 1 is obtained. Reaction of this imine with the mixed anhydride of trifluoroacetic acid and azidoacetic acid [Tetrahedron Lett., 2319 (1973)] gives methyl cis-1-(2,4-dimethoxybenzyl)-3-azido-4-oxo-2-azetidinecarboxylate (3). This reaction can be run as a two-step process by first generating the mixed anhydride and then adding this to a solution of the imine. Alternatively, a one step procedure can be used in which the azidoacetic acid is added to a solution of the imine followed by the addition of the trifluoroacetic anhydride. In addition, other glyoxalate esters such as ethyl or propyl can be used in the same manner.

The 2,4-dimethoxybenzyl group is removed by oxidative methods. For example, treatment of the N-(2,4-dimethoxybenzyl)β-lactam with potassium persulfate effects the deblocking reaction to generate the free β-lactam. This reaction is carried out in the presence of sodium monohydrogen phosphate. With some derivatives, pH control during the reaction within a range of 5–6 may be advantageous to the reaction yield. Under these conditions we have found that the benzyl group is not removed like the dimethoxybenzyl group. However, one skilled in the art could try other substituted benzyl moieties and determine if they are removable and therefore are also able to perform the same function as the dimethoxybenzyl group.

Reduction of the 2-alkoxycarbonyl group with suitable reducing agents such as sodium borohydride gives the 2-methyl alcohol derivative. In particular, the methoxycarbonyl group is readily reduced with sodium borohydride to give the alcohol derivative.

The alcohol derivative can also be prepared by reduction of the 2-carboxylic acid by standard reduction methods known in the art. The acid is prepared from the ester derivative by base hydrolysis. For example, the methyl ester hydrolyzes to the carboxylic acid by treatment with sodium carbonate, potassium carbonate or similar base. The carboxylic acid can be converted to its acid chloride and reduced with sodium borohydride to give the desired alcohol moiety. The 1-(2,4-dimethoxybenzyl)-2-carboxylic acid derivative can be reduced to the 2-methyl alcohol derivative which can be converted to the corresponding tosylate. The dimethoxybenzyl group can be removed at this point to give the β-lactam methyl tosylate precursor which can be carried further as has been described.

The alcohol is treated with p-toluenesulfonyl chloride, benzenesulfonyl chloride, p-bromobenzenesulfonyl chloride, mesyl chloride or similar reagents which convert the alcohol into a group which is readily displaced by iodide ion by nucleophilic displacement. Standard nucleophilic displacement of the sulfonate moiety with iodide followed by another nucleophilic displacement with sulfur derivatives gives the mercapto methyl moiety or a group which can be converted to the desired mercapto methyl compound. Triphenylmethylmercapto and p-methoxybenzylmercapto are typical groups which readily cleaved to the free mercapto group as set out above.

The new cephalosporin-like nucleus is generated by a cyclization reaction of the mercaptomethyl compound and a bromopyruvate derivative. The product formed contains a hydroxy group alpha to the carboxyl group. Dehydration of this hydroxy group places the double bond in the nucleus at the 2,3-position analogous to the cephalosporin series. Dehydration is best carried out with thionyl chloride and pyridine or trifluoroacetic anhydride.

The starting materials for the compounds of this invention are commercially available, prepared by known methods or described herein.

Also included within the scope of this invention is the pharmaceutically acceptable non-toxic salts of the active compounds or esters easily degraded to the active compound in vivo. These include the salts of the carboxylic acid at position 2 or within the acyl sidechain and the acid addition salts of any basic substituent present in the compound. Carboxylic acid salts include those where the cation is an alkali metal such as sodium or potassium, alkaline earth such as calcium, or an ammonium cation such as ammonium, cyclohexylamine and the like. The acid addition salts are prepared from those acids known and used in pharmaceutical preparations including both inorganic and organic acids. The salts are prepared by the standard methods well known in the art.

The compounds of this invention within Formulae I and II exist in the cis configuration at positions 6 and 7. The compounds also exist as optical isomers. Included within the scope of this invention is the separate optical isomers as well as any mixtures thereof.

The compounds of Formula I of this invention have antibacterial activity against both Gram-positive and Gram-negative bacteria. For example, 7-phenoxyacetamido-8-oxo-4-thia-1-azabicyclo[4.2.0]oct-2-ene-2-carboxylic acid has antibacterial activity against *Staphylococcus aureus* and *Shigella paradysenteriae*. The compound 7-(α-aminophenylacetamido)-8-oxo-4-thia-1-azabicyclo[4.2.0]oct-2-ene-2-carboxylic acid has additional activity against *Escherichia coli, Klebsiella pneumoniae, Serratia marcescens, Salmonella paratyphi, Shigella paradysenteriae,* and *Enterobacter* species. The compounds are useful for the treatment and prevention of bacterial infections as well as for sterilization of equipment, glassware and the like.

The compounds of Formula II and III are useful as chemical intermediates in the preparation of novel cephalosporin-like compounds of Formula I as has been described herein. Compounds within Formula II where W is amino ($NH_2$) can be acylated as described above with any of the acyl groups known in the cephalosporin or penicillin arts to give compounds which, after removal of any ester protecting group, have antibacterial activity. Compounds within Formula II where R' is an amino protecting group are useful to prepare the compounds where R' is hydrogen.

The following examples are presented to illustrate the invention but are not to be construed as limiting the scope thereof. All temperatures are in degrees Centigrade unless otherwise indicated.

PREPARATION 1

Methyl N-(2,4-dimethoxybenzyl)iminoacetate

To a mixture containing 16.82 g (0.101 mole) of 2,4-dimethoxybenzylamine and anhydrous magnesium sulfate in 150 ml of methylene chloride at 25° is added a solution of 10.05 g (0.114 mole) of methyl glyoxalate in 20 ml of methylene chloride. The reaction mixture is stirred at room temperature overnight (15 hours) and then is filtered and the solvents are removed in vacuo to afford the imine as a dark orange gum.

PREPARATION 2

4,5-Diphenyl-2-oxo-4-oxazolin-3-ylacetic acid chloride

A mixture of 4,5-diphenyl-2-oxo-4-oxazolin-3-ylacetic acid (2.1 g, 7.1 mmol) [*J. Org. Chem.*, 38, 3034 (1973)], thionyl chloride (5 ml) and methylene chloride (20 ml) is refluxed for 2.5 hours. After cooling to room temperature the solvent is removed in vacuo and resulting oil crystallizes on standing. The product is triturated with ether-hexane to give the title compound: 2.0 g mp 104°–112°.

PREPARATION 3

Bromopyruvate Esters

To a solution of 3.3 g (37.5 mmole) of pyruvic acid and 7.9 g (37.5 mmole) of trichloroethyl chloroformate in 200 ml of dry tetrahydrofuran at 0° is added dropwise 0.6 ml of pyridine. After stirring for 2 hrs. at room temperature, the mixture is concentrated in vacuum, diluted with water and extracted with ethyl acetate. The extract is washed with 5% HCl, dried over $MgSO_4$, evaporated and distilled in vacuum to give 4.0 g (50%) trichloroethyl pyruvate, bp 75°–82° (17 mm).

Trichloroethyl pyruvate (3.7 g, 17 mmole) is heated to 65° and 1.1 ml (17 mmole) of bromine is added dropwise over 1 hr. A stream of carbon dioxide is passed through the reaction mixture during the addition to remove the HBr formed in the reaction. The mixture is cooled to room temperature, diluted with water and extracted with ethyl acetate. The extract is dried over MgSO$_4$, evaporated and distilled in vacuum to give 1.8 g of trichloroethyl bromopyruvate, bp 74°–77° (0.01 mm).

Bromopyruvic acid is treated with diphenyldiazomethane by standard methods to give benzhydryl bromopyruvate.

The t-butyl ester is also prepared by standard methods by reacting O-t-butyl-N,N'diisopropylpseudourea [*Ann. Chem.*, 597, 235 (1955)] and bromopyruvic acid.

PREPARATION 4

3-Bromo-2-ketobutyrate esters

At room temperature under argon 1.85 g (9.6 mmol) of diphenyldiazomethane in 15 of dry benzene is added dropwise to a solution of 1.30 g (7.35 mmol) of 3-bromo-2-ketobutyric acid in 15 ml of dry benzene with vigorous stirring. Addition of the diazo compound is continued until a faint red color persisted (0.5 hr). The solvent is removed in vacuo and the yellow oil is dissolved in ether, filtered and concentrated to give 3.12 g crude benzhydryl ester. Chromatography on silica gel eluting with benzene affords 2.43 g (95%) pure benzhydryl 3-bromo-2-ketobutyrate as a yellow oil.

A solution of 1.6 g (8.85 mmol) of 3-bromo-2-ketobutyric acid and 7 g (4 equivalents) of 0-t-butyl-N,N'-diisopropylpseudourea in 14 ml methylene chloride in stirred overnight at room temperature. After filtration, the solution is washed with NaHCO$_3$ and brine, dried and evaporated to an oil which is chromatographed on silica gel with benzene as eluant to give 1 g (45%) of t-butyl 3-bromo-2-ketobutyrate.

EXAMPLE 1

Methyl cis-1-(2,4-Dimethoxybenzyl)-3-azido-4-oxoazetidine-2-carboxylate

Method A:

To a solution of 15.1 g (0.149 mole) of azidoacetic acid in 130 ml of anhydrous methylene chloride at 0° (ice bath) is added dropwise 21.0 ml (0.15 mole) of trifluoroacetic anhydride. This mixture is stirred at 0° for 15 min and then 20.8 ml (0.15 mole) of triethylamine is added dropwise. Stirring is continued for an additional 45 min and then the entire reaction mixture is transferred under argon into an addition funnel which is cooled externally by dry ice. The addition funnel is attached to a flask containing the imine from Preparation 1;200 ml of anhydrous methylene chloride, and 20.8 ml (0.15 mole) of triethylamine. The solution of the mixed anhydride is added dropwise from the addition funnel to the solution of imine at 0°. Stirring is continued at 0° for 1 hr and then the dark reaction mixture is transferred to a separatory funnel and washed with H$_2$O, aqueous NaHCO$_3$ and brine and then dried over anhydrous magnesium sulfate. The solvents are removed in vacuo and the residue is chromatographed on 300 g of silica gel (70–230 mesh) affording an off-white solid which is further purified by trituration with ether to give 14.45 g (45%) of the title product as a white solid; tlc: benzene: ethyl acetate (1:1), silica gel GF, Rf = 0.64. Recrystallization from ethyl acetate-hexane affords an analytical sample, mp 82°–84°.

Method B:

A solution of 1.6 g (9.55 mmol) dimethoxybenzylamine in 5 ml of CH$_2$Cl$_2$ is rapidly added at 0° to a solution of 1.06 g (10 mmol) freshly distilled methyl glyoxylate in 15 ml CH$_2$Cl$_2$. A slight exotherm occurred and water droplets appeared. Magnesium sulfate (5 g) is added and the mixture stirred at 0° for 2 hr. Fresh magnesium sulfate (1.0 g) is added, the magnesium sulfate removed by filtration under argon and washed with a minimum of CH$_2$Cl$_2$.

To a solution of 3.8 g (36 mmol) of azidoacetic acid (pumped in high vacuum 3 hr) in 125 ml of CH$_2$Cl$_2$ is added 10.6 ml (76 mmol) of triethylamine with cooling. Magnesium sulfate (3 gm) is added, the mixture stirred 10 min at room temperature, filtered under argon and washed with a 25 ml CH$_2$Cl$_2$.

The azidoacetic acid solution is added at 0° to the imine, sufficient methylene chloride is added to bring the total volume to 200 ml, the solution cooled to 0° under argon and 5.3 ml (38 mmol) trifluoroacetic anhydride added slowly over ½ hr with vigorous stirring and cooling. The mixture is stirred for 1 hr at 0°, allowed to warm to room temperature, transferred to a separatory funnel, washed with water, 5% NaHCO$_3$, 2% phosphoric acid and 5% NaHCO$_3$, dried over magnesium sulfate-charcoal; filtered and the filtrate is retreated twice with charcoal and evaporated to dryness. The residue is dissolved in a minimum of ether and stored at −20° to allow crystallization. The crystalline mass was isolated and washed with cold ether to give 1.9 gm (64%) product, mp 79°–80.5°.

EXAMPLE 2

Methyl cis-1-(2,4-Dimethoxybenzyl)-3-amino-4-oxoazetidine-2-carboxylate

A mixture containing 10.0 g (0.0312 mole) of methyl cis-1-(2,4-dimethoxybenzyl)-3-azido-4-oxoazetidine-2-carboxylate, 1.0 g of 10% palladium on carbon, and 200 ml of ethanol is hydrogenated for 2 hrs at 40°–45° and 60 psi of hydrogen. The reaction mixture is allowed to cool to 25° and is filtered through filter-air. After removing the solvents in vacuo a clear, yellow gum of the title product is obtained.

EXAMPLE 3

Methyl cis-3-t-Butoxycarbonylamino-1-(2,4-dimethoxybenzyl)-4-oxoazetidine-2-carboxylate A solution of 5.5 g (18.8 mmole) of methyl cis-3-amino-1-(2,4-dimethoxybenzyl)-4-oxoazetidine-2-carboxylate in 100 ml of dry toluene is cooled to −78°; 2.5 ml (18.8 mmole) of triethylamine is added followed by rapid addition of 35 ml (42 mmole) of a 12% solution of phosgene in benzene. The mixture is stirred 15 min at −78°, 3 hr at −45° (acetonitrile-dry ice), then warmed to room temperature and concentrated to half volume in vacuum. To the resulting solution is added 50 ml of t-butanol and the mixture is stirred at room temperature overnight. The solvents are removed in vacuum, the residue is diluted with ethyl acetate and filtered. The filtrate is transferred to a separatory funnel and washed with 5% NaHCO$_3$, 5% HCl and brine; dried over magnesium sulfate and evaporated to dryness. Recrystallization of the crude, crystalline product affords 3.8 g (52%) of the title compound. Recrystallization from ether gives an analytical sample.

EXAMPLE 4

Methyl cis-1-(2,4-Dimethoxybenzyl)-3-phthalimido-4-oxo-azetidine-2-carboxylate 2,4-Dimethoxybenzylamine (5.01 g, 0.03 mol) and methyl glyoxolate (3.17 g, 0.036 mol) are condensed as in Preparation 1 but at 0°-5° for 2 hours. The resulting imine is dissolved in methylene chloride (800 ml) and cooled in an ice bath. Triethylamine (5.4 ml) is added followed by the dropwise addition of a solution of N-phthalimido acetic acid chloride (7.54 g, 0.0338 mol) [*J. Amer. Chem. Soc.*, 71, 1856 (1949)] in methylene chloride (80 ml). After the reaction is stirred 2 hours, the solution is concentrated and then is washed with water, dilute HCl, and dilute $NaHCO_3$. The dried organic phase is evaporated to give the title product which is triturated with ether; 6.4 g (50%).

EXAMPLE 5

Methyl cis-1-(2,4-Dimethoxybenzyl)-3-(4,5-diphenyl-2-oxo-4-oxazolin-3-yl)-4-oxoazetidine-2-carboxylate The imine from Preparation 1 (1.43 g) is dissolved in dry methylene chloride (13 ml) and triethylamine (1 ml) and cooled in an ice bath. The acid chloride from Preparation 2 (2.0 g, 6.4 mmol) in methylene chloride (10 ml) is added over a 10-minute period. After 1 hour, the mixture is washed with water and 5% $NaHCO_3$, the dried solution is evaporated to a red oil which is chromatographed on 60 g of silica gel with 5% ethyl acetate in chloroform as eluant to give the title product, 2.37 g.

EXAMPLE 6

Methyl cis-1-(2,4-Dimethoxybenzyl)-3-phenoxyacetamido-4-oxo-2-azetidinecarboxylate The crude amine prepared in Example 2 from 10 g of the azido precursor is taken up in 100 ml of anhydrous methylene dichloride and is cooled to 0° in an ice bath. To this solution is added 4.32 ml (0.0312 mol) of triethylamine followed by the slow addition of a solution of 5.32 g (0.0312 mol) of phenoxyacetyl chloride in 40 ml of methylene dichloride. The mixture is stirred at 0° for 1 hr. then poured into a separatory funnel and extracted successively with water, aqueous HCl, aqueous $NaHCO_3$, brine and is dried over anhydrous magnesium sulfate. After filtration the solvent is removed in vacuo to give a yellow solid. This material is partially dissolved in ether, cooled to −25°, and filtered to afford 11.2 g (84%) of the title product as a white solid which is one spot on tlc: benzene-ethyl acetate (1:1), silica gel, Rf 0.38. An analytical sample, mp 115.5°–116.0°, is obtained by recrystallization from ethyl acetate-hexane.

EXAMPLE 7

When p-methoxybenzyl alcohol, isoborneol, benzyl alcohol, or 2,2,2-trichloroethanol is substituted for t-butanol in Example 3, methyl 3-(p-methoxybenzyloxycarbonylamino)-1-(2,4-dimethoxybenzyl)-4-oxoazetidine-2-carboxylate, methyl 3-(isobornyloxycarbonylamino)-1-(2,4-dimethoxybenzyl)-4-oxoazetidine-2-carboxylate, methyl 3-(benzyloxycarbonylamino)-1-(2,4-dimethoxybenzyl)-4-oxoazetidine-2-carboxylate, or methyl 3-(2,2,2-trichloroethoxycarbonylamino)-1-(2,4-dimethoxybenzyl-4-oxo-azetidine-2-carboxylate is obtained.

Methyl 3-(isobornyloxycarbonylamino)-1-(2,4-dimethoxybenzyl)-4-oxoazetidine-2-carboxylate can also be prepared by treating the 3-amino compound with isobornyloxycarbonyl chloride in the presence of base according to standard procedures; *Chem. Pharm. Bull.*, 20, 1017 (1972).

EXAMPLE 8

Methyl cis-3-t-Butoxycarbonylamino-4-oxoazetidine-2-carboxylate

A solution of 10.5 g (26.7 mmole) of methyl 3-t-butoxycarbonylamino-1-(2,4-dimethoxybenzyl)-4-oxoazetidine-2-carboxylate in 500 ml of acetonitrile is degassed with argon and warmed to 80°. A degassed solution of 15 g (55.5 mmole) of potassium persulfate and 7.5 g (28 mmole) of sodium monohydrogen phosphate in 150 ml of water is added in five portions over 1 hr. The reaction is stirred at 80°–85° under argon for 2–3 hrs until all starting material is consumed (tlc). The reaction mixture is cooled, concentrated in vacuum, shaken with ethyl acetate-water. The organic phase is washed with dilute HCl, $NaHCO_3$ solution and brine; dried over magnesium sulfate and evaporated to dryness. The residue is chromatographed over silica gel with 1:1 benzene-ethyl acetate to afford pure product which crystalized from ethyl acetate-hexane to yield 2.0 g (31%) of the title compound. A less pure fraction from the column, is crystallized from ethyl acetate-hexane to give an additional 0.5 g of product, overall yield, 38%.

EXAMPLE 9

When the products of Examples 1, 4, 5, 6 and 7 are treated with potassium persulfate and sodium monohydrogen phosphate according to the procedure of Example 8 the following products are obtained:

methyl cis-3-azido-4-oxoazetidine-2-carboxylate; 72% yield mp 77°–78°
methyl cis-3-phthalimido-4-oxoazetidine-2-carboxylate; 40% yield
methyl cis-3-(4,5-diphenyl-2-oxo-4-oxazolin-3-yl)-4-oxoazetidine-2-carboxylate, 32% yield
methyl cis-3-phenoxyacetamido-4-oxoazetidine-2-carboxylate; 69% yield, mp 140°–41°
methyl cis-3-isobornylcarbonylamino-4-oxo-azetidine-2-carboxylate
methyl cis-3-(p-methoxybenzyloxycarbonylamino)-4-oxoazetidine-2-carboxylate
methyl cis-3-(benzyloxycarbonylamino)-4-oxoazetidine-2-carboxylate
methyl cis-3-(2,2,2-trichloroethoxycarbonylamino)-4-oxoazetidine-2-carboxylate

EXAMPLE 10

Methyl cis-3-Amino-4-oxoazetidine-2-carboxylate

A solution of methyl cis-3-azido-4-oxoazetidine-2-carboxylate (8.5 g, 50 mmol) and an equivalent of p-toluenesulfonic acid in 200 ml of ethanol is hydrogenated for 3 hours over 1 g of 10% Pd on carbon at 40 psi. The solution is filtered and the filtrate is evaporated to title product or the tosylate salt which can be converted to the free base by standard methods.

EXAMPLE 11

A solution of anhydrous $K_2CO_3$ (249 mg, 1.8 mmol) in tetrahydrofuran (8 ml) and water (12 ml) is degassed with argon and then methyl cis-3-phenoxyacetamido-1-(2,4-dimethoxybenzyl)-4-oxoazetidine-2-carboxylate (150 mg, 0.35 mmol) is added. The reaction is stirred 1.5 hours at room temperature, the organic solvent is evaporated and the aqueous layer is acidified and extracted with methylene chloride. The dried extracts are evaporated to give a solid which is recrystallized from ethyl acetate-hexane to give pure cis-3-phenoxyacetamido-1-(2,4-dimethoxybenzyl)-4-oxoacetidine-2-carboxylic acid, mp 169°–170° (d).

Methyl cis-3-phenoxyacetamido-4-oxoazetidine-2-carboxylate is treated with $K_2CO_3$ in methanol-water as above to give cis-3-phenoxyacetamido-4-oxoazetidine-2-carboxylic acid, mp 150°–51° from ethyl acetate.

EXAMPLE 12 cis-3-t-Butoxycarbonylamino-2-hydroxymethyl-4-oxoazetidine

A solution of 2.0 g (8.2 mmole) of methyl 3-t-butoxycarbonylamino-4-oxoazetidine-2-carboxylate in 20 ml of tetrahydrofuran is cooled in ice and a solution of 0.75 g (20 mmole) of sodium borohydride in 10 ml of water is added. The mixture is stirred 20 min at 0° and then 1.5 hr. at room temperature. Acetic acid is added dropwise to decompose the excess borohydride and the mixture is concentrated in vacuum. The residue is diluted with brine and extracted with ethyl acetate. The organic phase is washed with brine and 5% $NaHCO_3$; dried over magnesium sulfate and evaporated to dryness to give 0.9 g (50%) of the title product as white crystals, mp 128°–131°.

EXAMPLE 13

When the 3-azido, 3-oxazolinyl, 3-phenoxyacetamido, 3-isobornyloxycarbonylamino, 3-(p-methoxybenzyloxycarbonylamino, and 3-benzyloxycarbonylamino compounds from Example 9 are reduced with sodium borohydride by the procedure of Example 12 the following products are obtained;

cis-3-azido-2-hydroxymethyl-4-oxoazetidine; 56% yield
cis-2-hydroxymethyl-3-(4,5-diphenyl-2-oxo-4-oxazolin-3-yl)-4-oxoazetidine; ca. 100% yield
cis-2-hydroxymethyl-3-phenoxyacetamido-4-oxo-azetidine; 68% yield, mp. 153°–4° (from ethyl acetate)
cis-2-hydroxymethyl-3-isobornyloxycarbonyl-4-oxoazetidine
cis-2-hydroxymethyl-3-(p-methoxybenzyloxycarbonylamino)-4-oxoazetidine
cis-3-benzyloxycarbonylamino-2-hydroxymethyl-4-oxoazetidine

EXAMPLE 14 cis-3-t-Butoxycarbonylamino-4-oxo-2-azetidinylmethyl tosylate

To a solution of 0.9 g (4.3 mmole) of 98% p-toluenesulfonyl chloride in 10 ml of dry pyridine at 0° is added 0.9 g (4.15 mmole) of 3-t-butoxycarbonylamino-2-hydroxymethyl-4-oxoazetidine. The mixture is stirred for 2 hr at 0° and then stored at 5° overnight. After addition of 0.5 ml of 85% lactic acid, the mixture is stirred for 1 hr, poured into ethyl acetate and washed with dilute HCl, 5% $NaHCO_3$, and brine. The extract is dried over magnesium sulfate and evaporated to dryness to give 1.1 g (70%) of crystalline title product. Recrystallization from hexane-ethyl acetate gives an analytical sample, mp 160°–162° (d).

EXAMPLE 15

Treatment of the products obtained in Example 13 with p-toluenesulfonyl chloride according to the procedure of Example 14 gives the corresponding tosylates:

cis-3-azido-4-oxo-2-azetidinylmethyl tosylate; 80% yield mp 87°–89°
cis-3-(4,5-diphenyl-2-oxo-4-oxazolin-3-yl)-4-oxo-2-azetidinylmethyl tosylate
cis-3-phenoxyacetamido-4-oxo-2-azetidinylmethyl tosylate; 71% yield, mp 136° (d)
cis-3-isobornyloxycarbonylamino-4-oxo-2-azetidinylmethyl tosylate
cis-3-(p-methoxybenzyloxycarbonylamino)-4-oxo-2-azetidinylmethyl tosylate
cis-3-benzyloxy carbonylamino-4-oxo-2-azetidinylmethyl tosylate When cis-2-hydroxymethyl-1-(2,4-dimethoxybenzyl)-3-(4,5-diphenyl-2-oxo-4-oxazolin-3-yl)-4-oxoazetidine is reacted according to Example 13 except that mesyl chloride is substituted for p-toluenesulfonyl chloride, cis-3-(4,5-diphenyl-2-oxo-4-oxazolin-3-yl)-4-oxo-2-azetidinylmethyl mesylate is obtained; 73% yield, mp 185°–8° from ethyl acetate-hexane.

EXAMPLE 16 cis-3-Amino-4-oxo-2-azetidinylmethyl tosylate

A solution of cis-3-azido-4-oxo-2-azetidinylmethyl tosylate (5.0 g) in 50% aqueous acetic acid (50 ml) is cooled and then treated with zinc dust (2.0 g). The reaction is stirred for 30 minutes, filtered, and the solid washed with $H_2O$ (50 ml). The filtrate is saturated with $H_2S$ over ½ hour, the zinc sulfide is removed by filtration and the filtrate evaporated to near dryness. The residue is dissolved in ethyl acetate-water and adjusted to pH 10. Phases are separated and the aqueous layer is extracted with ethyl acetate. The dried organic phases are evaporated to give the amino compound; 3.0 g (66%).

EXAMPLE 17

A mixture of the 3-amino tosylate compound from Example 16 (0.14 g), N-t-butoxycarbonylphenylglycine (0.16 g) and dicyclohexylcarbodiimide (0.12 g) in methylene chloride (5 ml) is stirred one hour at 0° C. The solid is removed by filtration and the filtrate is evaporated to dryness. The residue is chromatographed on silica gel with 80:20 ethyl acetate-benzene as eluant to give cis-3-(α-t-butoxycarbonylaminophenylacetamido)-4-oxo-2-azetidinylmethyl tosylate; 0.19 g (17%).

2-Thienylacetic acid, the 3-amino derivative from Example 16, and dicyclohexylcarbodiimide (3.7 mmol of each) is reacted in methylene chloride as above. The mixture is diluted with ethyl acetate (150 ml) and filtered; the filtrate is washed with 5% $NaHCO_3$, dilute HCl, and brine, dried, evaporated and crystallized from acetone-ether to give cis-3-(2-thienylacetamido)-4-oxo-2-azetidinylmethyl tosylate; 0.9 g (69%) mp 121°–124°.

The 3-amino derivative is acylated with 0-formylmandelic acid chloride in the presence of triethylamine to give cis-3-formylmandelamido-4-oxo-2-azetidinyl methyl tosylate, 98% mp 111°–113° (dec).

EXAMPLE 18 cis-3-Phenoxyacetamido-4-oxo-2-azetidinemethyl iodide

A mixture containing 13.68 g (33.9 mmol) of cis-3-phenoxyacetamido-4-oxo-2-azetidinemethyl tosylate, 39.8 g (0.265 mol) of sodium iodide and 550 ml of acetone is heated at reflux for a period of 6 hr and then is allowed to cool to ambient temperature. The acetone is removed in vacuo and the residue is suspended in ethyl acetate and extracted withwater, sodium thiosulfate and brine. The dried ethyl acetate solution was evaporated in vacuo to give a yellow semi-crystalline residue. Recrystallization from ethyl acetate resulted in 10.3 g (84%) of crystalline product; mp 150° (dec).

EXAMPLE 19

When the appropriate tosylate or mesylate which are disclosed in Example 14, 15 and 17 is treated with sodium iodide by the procedure disclosed in Example 18 the following products are obtained:

cis-3-t-butoxycarbonylamino-4-oxo-2-azetidinylmethyl iodide
cis-3-azido-4-oxo-2-azetidinylmethyl iodide
cis-3-(4,5-diphenyl-2-oxo-4-oxazolin-3-yl)-4-oxo-2-azetidinylmethyl iodide
cis-3-(α-t-butoxycarbonylaminophenylacetamido)-4-oxo-2-azetidinylmethyl iodide, 78% yield
cis-3-thienylacetamido-4-oxo-2-azetidinylmethyl iodide, 98% yield
cis-3-formylmandelamido-4-oxo-2-azetidinylmethyl iodide
cis-3-isobornyloxycarbonylamino-4-oxo-2-azetidinylmethyl iodide
cis-3-(p-methoxybenzyloxycarbonylamino)-4-oxo-2-azetidinylmethyl iodide
cis-3-benzyloxycarbonylamino-4-oxo-2-azetidinylmethyl iodide

EXAMPLE 20

3-t-Butoxycarbonylamino-4-oxo-2-(p-methoxybenzylthiomethyl)-azetidine

To a solution of 1.1 g (2.97 mmole) of 3-N-t-butoxycarbonylamino-4-oxo-2-azetidinylmethyl tosylate in 15 ml of dry dimethylformamide under argon was added 4.0 g (26 mmole) of sodium iodide. The mixture was heated to 65° for 4 hours, then stirred at room temperature overnight. The resulting suspension was diluted with 50 ml of ethyl acetate, filtered, concentrated in vacuum, flushed with argon and 3.0 ml of p-methoxybenzyl mercaptan and 2.0 ml of triethylamine were added. The mixture was stirred at room temperature for 18 hours and then poured into ice water-ethyl acetate. The organic phase was separated and washed with water, 5% NaHCO$_3$ and brine; dried over magnesium sulfate and evaporated to dryness. The residue was chromatographed over silica gel with 1:1 benzene-ethyl acetate to afford after evaporation and crystallization from ethyl acetate-hexane, 335 mg (32%) of pure product, mp 120°–123°.

EXAMPLE 21

When an appropriate iodide derivative is reached with p-methoxybenzyl mercaptan (2 equivalents) in the presence of triethylamine (2equivalents) according to the procedure set forth in Example 20 the following compounds are obtained cis-3-phenoxyacetamido-4-oxo- 2-(p-methoxybenzylthiomethyl)azetidine; mp 139°–41°
cis-3-formylmandelamido-4-oxo-2-(p-methoxybenzylthiomethyl)azethidine
cis-3-(α-t-butoxycarbonylaminophenylacetamido)-4-oxo-2-(p-methoxybenzylthiomethyl)azetidine
cis-3-isobornylcarbonylamino-4-oxo-2(p-methoxybenzylthiomethyl)azetidine
cis-3-(p-methoxybenzyloxycarbonylamino)-4-oxo-2-(p-methoxybenzylthiomethyl)azetidine
cis-3-benzyloxycarbonylamino-4-oxo-2-(p-methoxybenzylthiomethyl)azetidine

EXAMPLE 22 cis-3-(2-Thienylacetamido)-4-oxo-2-(triphenylmethylthiomethyl)azetidine

To a solution of 0.8 g (2.3 mmole) of cis-3-(2-thienylacetamido)-4-oxo-2-azetidinemethyl iodide and 0.9 g (9 mmole) of triethylamine in 10 ml of dry dimethylformamide is added 1.27 g (4.6 mmole) of triphenylmethanethiol. The mixture is stirred under argon overnight, diluted with 100 ml of ethyl acetate and washed with dliute HCl and water. After drying with magnesium sulfate, the extract is evaporated to dryness and the residue triturated with ether. The crystalline product is filtered and dried to give the title compound.

EXAMPLE 23

When the methyl iodide derivatives of Examples 18 and 19 are reacted with triphenylmethanethiol according to the procedure of Example 22 the following compounds are obtained.

cis-3-phenoxyacetamido-4-oxo-2-(triphenylmethylthiomethyl)azetidine
cis-3-t-butoxycarbonylamino-4-oxo-2-(triphenylmethylthiomethyl)azetidine
cis-3-(4,5-diphenyl-2-oxo-4-oxazolin-3-yl)-4-oxo-2-(triphenylmethylthiomethyl)azetidine
cis-3-(α-t-butoxycarbonylaminophenylacetamido)-4-oxo-2-(triphenylmethylthiomethyl)azetidine
cis-3-formylmandelamido-4-oxo-2-(triphenylmethylthiomethyl)azetidine
cis-3-isobornyloxycarbonylamino-4-oxo-2-(triphenylmethylthiomethyl)azetidine
cis-3-(p-methoxybenzyloxycarbonylamino)-4-oxo-2-(triphenylmethylthiomethyl)azetidine
cis-3-benzyloxycarbonylamino-4-oxo-2-(triphenylmethylthiomethyl)azetidine

EXAMPLE 24

3-t-Butoxycarbonylamino-4-oxo-2-mercaptomethylazetidine

To a solution of 335 mg (0.95 mmole) of 3-t-butoxycarbonylamino-4-oxo-2-(p-methoxybenzylthiomethyl)-azetidine in 5 ml of methanol and 20 ml of methylene chloride is added 1.7 g (5.3 mmole) of mercuric acetate. The mixture is stirred 24 hours under argon, diluted with excess ether and the precipitated mercury adduct filtered and wshed well with ether. The mercury complex is suspended in water, layered with ethyl acetate and hydrogen sulfide gas is passed through the mixture for 1 hour. The mercuric sulfide is removed by filtration, the ethyl acetate layer is separated and washed with brine, dried over magnesium sulfate and evaorated to dryness. Trituration of the residue with 1:1 ethyl acetate-hexane gives 122 mg (55%) of the crystalline title product.

EXAMPLE 25 cis-3-(2-Thienylacetamido)-4-oxo-2-mercaptomethylazetidine

To a solution of 0.1 g (0.2 mmole) of cis-3-(2-thienylacetamido)-4-oxo-2-(triphenylmethylthiomethyl)-azetidine in 3 ml of methanol is added a solution containing 34 mg (0.2 mmole) of silver nitrate and 16 mg (0.2 mmole) of pyridine. A percipitate of the silver mercaptide is formed immediately. Hydrogen sulfide gas is passed through the mixture for 5 minutes, the silver sulfide removed by filtration and the filtrate diluted with ethyl acetate and washed with dilute HCl and brine. The extract is dried and evaporated to dryness; trituration with ether gives the title compound as white crystals.

EXAMPLE 26

When the p-methoxybenzylthiomethyl derivatives prepared in Example 21 are deblocked according to the procedure of Example 24 the following compounds are obtained.

cis-3-phenoxyacetamido-4-oxo-2-mercaptomethylazetidine
cis-3-formylmandelamido-4-oxo-2-mercaptomethylazetidine
cis-3-(α-t-butoxycarbonylaminophenylacetamido)-4-oxo-2-mercaptomethylazetidine
cis-3-isobornyloxycarbonylamino-4-oxo-2-mercaptomethylazetidine
cis-3-(p-methoxybenzyloxycarbonylamino)-4-oxo-2-mercaptomethylazetidine
cis-3-benzyloxycarbonylamino-4-oxo-2-mercaptomethylazetidine Similarly when the triphenylmethylthiomethyl derivatives prepared in Example 23 are deblocked by the procedure set forth in Example 25 the corresponding mercaptomethyl compounds are obtained.

EXAMPLE 27

A solution methyl cis-3-(4,5-diphenyl-2-oxo-4-oxazolin-3-yl)-4-oxoazetidine-2-carboxylate(2.0 g, 3.9 mmol) in 50 ml ethanol is added to 10% Pd on carbon (0.5 g) which is premoistened with 2 ml 2N HCl. The mixture is hydrogenated for 12 hours at 50 psi and 40° C. After filtration, the solvent is removed and the oil is dissolved in methylene chloride which is then washed with NaHCO$_3$ and brine and dried. The solution is evaporated to give methyl cis-3-amino-1-(2,4-dimethoxybenzyl)-4-oxoazetidine-2-carboxylate.

EXAMPLE 28

Trichloroethyl 7α-t-Butoxycarbonylamino-6βH-2-hydroxy-8-oxo-4-thia-1-azabicyclo[4.2.0]octane-2-carboxylate To a suspension of 122 mg (0.52 mmole) of cis 3-t-butoxycarbonylamino-4-oxo-2-mercaptomethylazetidine in 20 ml of methylene chloride is added 156 mg (0.52 mmole) of trichloroethyl bromopyruvate followed at 0° by 50 μl of triethylamine. Methanol (5 ml) is added to effect solution and the mixture is stirred at room temperature for 1 hour. The solvents is removed in vacuum, the residue is dissolved in ethyl acetate which is washed with dilute HCl 5% NaHCO$_3$ and brine; dried over magnesium sulfate and evaporated to dryness. The residue is chromatographed over silica gel with 1:2 ethyl acetatebenzene to afford 80 mg (35%) of the title product as a mixture of diastereomers.

EXAMPLE 29

Trichloroethyl 7β-amino-6αH-8oxo-4-thia-1-azabicyclo-[4.2.0]oct-2-ene-2-carboxylate Method A:

To a solution of 70 mg (0.156 mmole) of the product from Example 28 in 3 ml of dry ethyl acetate is added 0.2 ml pyridine and 150 mg of methanesulfonyl anhydride. The mixture is stirred overnight at room temperature and then diluted with water. The aqueous solution is extracted with ethyl acetate and the extracts are washed with dilute HCl and 5% NaHCO$_3$ and then dried. Evaporation gives a residue which is chromatographed on silica gel with 80:20 benzene-ethyl acetate as eluant. The product (50 mg) is a mixture of the desired trichloroethyl cis-7-t-butoxycarbonylamino-8-oxo-4-thia-1-azabicyclo-[4.2.0]oct-2-ene-2-carboxylate and the 7-methylsulfonylamino derivative but separation before the following deblocking reaction is not necessary.

The above mixture is dissolved in 2 ml of methylene chloride, cooled to 0° and treated with 0.5 ml trifluoroacetic acid for 0.5 hr at 0°. The solution is washed with 5% NaHCO$_3$ and then extracted with dilute HCl. The aqueous phase is neutralized and extracted with ethyl acetate. The extracts are dried and then acidified with ethereal HCl. The hydrochloride salt of the title product is collected.

Method B:

To a solution of the product from Example 28 (150 mg) in ethyl acetate (4 ml) is added pyridine (150 μl). The solution is cooled to −10° C, stirred 1 hour with thionyl chloride (50 μl), diluted with water, acidified and extracted with ethyl acetate. The extracts are washed with 5% NaHCO$_3$, and brine, dried and evaporated. The product is purified and deblocked as in Method A.

EXAMPLE 30

When cis-3-t-butoxycarbonylamino-4-oxo-2-mercaptomethylazetidine is condensed with benzhydryl bromopyruvate by the procedure of Example 28, benzhydryl 7β-t-butoxycarbonylamino-6αH-2-hydroxy-8-oxo-4-thia-1-azabicyclo[4.2.0]octane-2-carboxylate is obtained. Dehydration by either of the methods set forth in Example 29 gives benzhydryl 7β-t-butoxycarbonylamino-6αH-8-oxo-4-thia-1-azabicyclo[4.2.0]oct-2-ene-2-carboxylate.

Similarly as described above, use of t-butyl bromopyruvate gives the two compounds described above as their t-butyl ester.

EXAMPLE 31

7β-Amino-6αH-8-oxo-4-thia-1-azabicyclo[4.2.0]oct-2-ene-2-carboxylic acid

Method A

To a solution of 43 mg (0.1 mmole) of trichloroethyl cis-7-t-butoxycarbonylamino-8-oxo-4-thia-1-azabicyclo[4.2.0]oct-2-ene-2-carboxylate in 6 ml of dimethylformamide and 6 ml of acetic acid is added over a 1.5 hr period 250 mg (3.8 mmole) zinc dust. The mixture is stirred vigorously for 3 hrs and then diluted with 50 ml of water. The mixture is acidified with dilute HCl, filtered and extracted with ethyl acetate. The organic phase is extracted with 5% NaHCO$_3$ which is acidified and reextracted into ethyl acetate. The final extracts are washed with brine, dried, and evaporated to give cis-7-butoxycarbonylamino-8-oxo-4-thia-1-azabicyclo[4.2.0]oct-2-ene-2-carboxylic acid.

The above product is dissolved in methylene chloride and treated with trifluoroacetic acid as outlined in Example 29. The reaction is evaporated in vacuo and the residue is triturated with ether to give the trifluoroacetate salt of the title product. The salt is dissolved in water and treated with basic ion-exchange resin ("Amberlite IR-45") until constant pH is obtained. After filtration, the aqueous solution is lyophilized to give the title product.

Method B

The ethyl acetate solution of trichloroethyl cis-7β-amino-6αH-8-oxo-4-thia-1-azabicyclo[4.2.0]oct-2-ene-2-carboxylate from Example 29 is treated with acetic acid and zinc dust as described above in Method A. After stirring 3 hrs, the reaction solution is acidified to pH 2 with dilute HCl, filtered, and evaporated to dryness. The residue is treated with basic ion-exchange as in Method A to give the title product.

Method C

A solution of benzhydryl 7β-t-butoxycarbonylamino-6αH-8-oxo-4-thia-1-azabicyclo[4.2.0]oct-2-ene-2-carboxylate (1 mmol) in methylene chloride is treated with trifluoroacetic acid at 0° as in Example 29, to cleave the two blocking groups and give the title compound.

EXAMPLE 32

Benzhydryl 7β-phenoxyacetamido-6αH-2-hydroxy-3-methyl-8-oxo-4-thia-1-azabicyclo[4.2.0]octane-2-carboxylate To a stirred solution of 0.234 g (0.88 mmol) of cis-3-phenoxyacetylamino-4-oxo-2-mercaptomethylazetidine and 0.304 g (0.88 mmol) benzhydryl 3-bromo-2-ketobutyrate in 26 ml of dry methylene chloride is added 122 μl (0.88 mmol) of triethylamine at room temperature under argon. The solution is stirred for 1 hr, then the methylene chloride is removed in vacuo and the residue dissolved in ethyl acetate. The ethyl acetate solution is washed with 3N HCl solution, 5% NaHCO$_3$ solution and saturated NaCl solution. After drying, the solution is evaporated in vacuo to give 0.531 g of crude product. Chromatography of 0.466 g of crude product on silica gel eluting with ethyl acetatehexane affords 320 mg of benzhydryl 7β-phenoxyacetamido-6αH-2-hydroxy-3-methyl-8-oxo-4-thia-1-azabicyclo[4.2.0]octane-2-carboxylate as a foam. (78%)

EXAMPLE 33

Benzhydryl 7β-phenoxyacetamido-6αH-3-methyl-8-oxo-4-thia-1-azabicyclo[4.2.0]oct-2-ene-2-carboxylate To a stirred solution of 0.200 g (0.39 mmol) of benzhydryl 7β-phenoxyacetamido-6α-2-hydroxy-3-methyl-8-oxo-4-thia-1-azabicyclo[4.2.0]octane-2-carboxylate and 282 μl trifluoroacetic anhydride in 4 ml of dry ethyl acetate is added dropwise 161 μl (2.0 mmol) pyridine at 0° under argon. The solution is allowed to come to room temperature and stirred for 20 hours. The reaction mixture is diluted with ethyl acetate and washed twice with 5% NaHCO$_3$, 3N HCl, and brine, The ethyl acetate layer is dried over MgSO$_4$ and concentrated in vacuo to afford 300 mg crude product. Chromatograhy on silica gel eluting with 50:50 ethyl acetate/benzene gives 21.8 mg (11%) of white, crystalline benzhydryl 7β-phenoxyacetamido-6αH-3-methyl-8-oxo-4-thia-1-azabicyclo[4.2.0]oct-2-ene-2-carboxylate and 42.1 mg (21%) of recovered starting material mp 155°–156°.

EXAMPLE 34

7β-Phenoxyacetamido-6αH-3-methyl-8-oxo-4-thia-1-azabicyclo[4.2.0]oct-2-ene-2-carboxylic acid A solution of 0.062 g (1.2 × 10$^{-4}$ mol) of benzhydryl 7β-phenoxyacetamido-6αH-3-methyl-8-oxo-4-thia-1-azabicyclo[4.2.0]oct-2-ene-2-carboxylate, 125 μl anisole, and 0.7 ml of trifluoroacetic acid in 2 ml of methylene chloride is stirred at 0° under argon for 1.3 hours. The trifluoroacetic acid and methylene chloride are removed in vacuo and the residue is treated with ethyl acetate and dilute HCl. The ethyl acetate is extracted with 5% NaHCO$_3$, and the aqueous combined extracts acidified to a pH of 1.5 and reextracted into ethyl acetate. The combined organic extracts are dried over MgSO$_4$, filtered and concentrated. After pumping under high vacuum, 25.2 mg of a yellow solid is isolated. Precipitating from methylene chloride-hexane solution afforded 18.7 mg (44%) of analytically pure title compound, mp 205-15 (dec).

EXAMPLE 35 t-Butyl 7β-phenoxyacetamido-6αH-2-hydroxy-3-methyl-8-oxo-4-thia-1-azabicyclo[4.2.0]octane-2-carboxylate To a stirred solution of 0.083 g (0.31 mmol) of cis-3-phenoxyacetamido-4-oxo-2-mercaptomethylazetidine and 0.084 g (0.31 mmol) t-butyl 3-bromo-2-ketobutyrate in 10 ml of dry methylene chloride is added 44 μl (0.31 mmol) of triethylamine at room temperature under argon. The solution is stirred for 1.25 hours, the methylene chloride removed in vacuo, and the residue dissolved in ethyl acetate. The ethyl acetate is washed with 3N HCl, 5% NaHCO$_3$ and brine. After drying, the solution is evaporated in vacuo in give 0.120 g of crude product. Chromatography on silica gel eluting with 50:50 ethyl acetate-hexane gives 93.8 mg (70%) of a colorless oil. After standing at room temperature, the oil solidified to give crystalline title compound, mp 138-150°.

EXAMPLE 36 t-Butyl 7β-phenoxyacetamido-6αH-3-methyl-8-oxo-4-thia-1-azabicyclo[4.2.0]oct-2-ene-2-carboxylate To a stirred solution of 0.302 g (0.72 mmol) of the 2-hydroxy compound from Example 35 and 200 μl (1.43 mmol) of trifluoroacetic anhydride in 6 ml dry ethyl acetate is added dropwise 290 μl (3.58 mmol) of pyridine at 0° under argon. The solution is allowed to come to room temperature and stir overnight (20 hrs). The reaction mixture is diluted with ethyl acetate and washed with 5% NaHCO$_3$, 3N HCl and brine. The ethyl acetate solution is dried over MgSO$_4$ and concentrated. Chromatography on silica gel eluting with ethyl acetate-hexane mixture affords 49.5 mg (17%) of the title compound as a yellow solid, mp 147°–149°.

EXAMPLE 37

Substitution of cis-3-t-butoxycarbonylamino-4-oxo-2-mercaptomethylazetidine for the phenoxyacetamido derivative in the procedures of Examples 33 and 35 gives the benzhydryl and t-butyl esters of 7β-t-butoxycarbonylamino-6αH-2-hydroxy-3-methyl-8-oxo-4-thia-1-azabicyclo[4.2.0]octane-2-carboxylic acid.

The above esters are each treated with trifluoroacetic anhydride by the procedure in Examples 33 and 36 or with the other dehydrating agents set forth in Example 29 to give benzhydryl and t-butyl 7β-t-butoxycarbonylamino-6αH-3-methyl-8-oxo-4-thia-1-azabicyclo[4.2.0]oct-2-ene-2-carboxylate.

Treatment of either of the above esters with trifluoroacetic acid by the procedure in Example 34 gives 7β-amino-6αH-3-methyl-8-oxo-4-thia-1-azabicyclo[4.2.0]oct-2-ene-2-carboxylic acid.

EXAMPLE 38 t-Butyl
7β-Phenoxyacetamido-6αH-3-bromomethyl-8-oxo-4-thia-1-azabicyclo[4.2.0]oct-2-ene-2-carboxylate A suspension of 30.0 mg (0.075 mmol) of t-butyl cis-7β-phenoxyacetamido-6αH-3-methyl-8-oxo-4-thia-1-azabicyclo[4.2.0]oct-2-ene-2-carboxylate and 28 mg (0.15 mmol) of N-bromosuccinimide in 5 ml of carbon tetrachloride is degassed, a trace of azobisisobutyronitrile is added and the mixture refluxed for 2 hrs. After cooling, the mixture is filtered, evaporated to dryness, redissolved in ethyl acetate, washed with 5% sodium bisulfite, dried over magnesium sulfate and evaporated to dryness. The residue was chromatographed on silica gel with 5% ethyl acetate in chloroform to give on trituration with methylene chloride-hexane, 10.8 mg of the title compound as a pale yellow amorphous solid.

EXAMPLE 39

7β-Phenoxyacetamido-6αH-3-acetoxymethyl-8-oxo-4-thia-1-azabicyclo[4.2.0]oct-2-ene-2-carboxylic acid A mixture of 48 mg (0.1 mmole) of the bromomethyl derivative from Example 38 and 200 mg of silver acetate in 10 ml of acetone is stirred at room temperature for 1 day. The mixture is filtered, the filtrate is evaporated to dryness and chromatographed over silica gel with 5% ethyl acetate in chloroform to afford the t-butyl ester of the title compound.

The above material is dissolved in ice cold trifluoroacetic acid containing 10% anisole. The solution is stirred at 0° for ½ hr, the solvent is removed in vacuum, the residue is dissolved in ethyl acetate and extracted with 5% sodium bicarbonate solution. The aqueous extract is carefully acidified and extracted with ethyl acetate, the extract is dried over magnesium sulfate and evaporation to dryness. Trituration with hexane affords the title compound.

EXAMPLE 40

When the t-butyl 7β-t-butoxycarbonylamino-6αH-3-methyl-8-oxo-4-thia-1-azabicyclo[4.2.0]oct-2-ene-2-carboxylate is treated with N-bromosuccinimide by the procedure of Example 38, t-butyl 7β-t-butoxycarbonylamino-6αH-3-bromomethyl-8-oxo-4-thia-1-azabicyclo[4.2.0.]oct-2-ene-2-carboxylate is obtained.

Treatment of the above bromomethyl derivative with sodium acetate or silver acetate according to the procedure of Example 39 gives t-butyl 7β-t-butoxycarbonylamino-6αH-3-acetoxymethyl-8-oxo-4-thia-1-azabicyclo[4.2.0]oct-2-ene-2-carboxylate When the above compound is treated with trifluoroacetic acid by the procedure of Example 39, 7β-amino-6αH-3-acetoxymethyl-8-oxo-4-thia-1-azabicyclo[4.2.0]oct-2-ene-2-carboxylic acid is obtained.

EXAMPLE 41

Trichloroethyl
7β-Phenoxyacetamido-6αH-2-hydroxy-8-oxo-4-thia-1-azabicyclo[4.2.0]octane-2-carboxylate To a solution of 273 mg (1.02 mmol) of cis-3-phenoxyacetamido-4-oxo-2-mercaptomethylazetidine and 305 mg (1.02 mmol) of trichloroethyl bromopyruvate in 30 ml of methylene chloride is added slowly at 0°, 0.110 ml triethylamine. After stirring for 2 hours at room temperature, the mixture is evaporated to dryness, the residue is dissolved in ethyl acetate, washed with 5% HCl, 5% NaHCO₃, and saturated NaCl, evaporated to dryness and chromatographed over silica gel with 1:1 ethyl acetate–hexane as eluant to give the title product, 256 mg (52%)

EXAMPLE 42

7β-Phenoxyacetamido-6αH-8-oxo-4-thia-1-azabicyclo[4.2.0.]oct-2-ene-4-carboxylic acid To a cooled solution (0° C) of 0.477 g (1 mmol) of trichloroethyl 7β-phenoxyacetamido-6αH-2-hydroxy-8-oxo-4-thia-1-azabicyclo[4.2.0.]octane-2-carboxylate in 10 ml ethyl acetate is added 65 μl of trifluoroacetic anhydride and then 362 μl of pyridine. The reaction is stirred overnight at room temperature and then diluted with ethyl acetate. The solution is washed with NaHCO₃ solution, 3N HCl and saturated saline solution. The dried solution is evaporated to give the ester of the title product which is recrystallized from benzene; 157 mg (34%).

In 24 ml solution of dimethylformamide-glacial acetic acid (1:1) is dissolved 70 mg of the above ester. To this solution is added over a 1.5 hour period 500 mg of zinc dust which has been treated with 5% HCl for 3 minutes, washed with water, ethanol, and ether and then dried. The reaction mixture is stirred 3 hours at room temperature, diluted with water, acidified with 3N HCl and extracted with ethyl acetate. The extracts are washed with a large volume of 5% NaHCO₃. The aqueous solution is acidified to pH 2 with HCl and extracted with ethyl acetate. The dried extracts are concentrated in vacuo and then high vacuum is used to remove residual acetic acid. The residue is triturated with ether-hexane, dissolved in methylene chloride and precipitated with hexane to give the title product, mp 194°–5° (dec).

EXAMPLE 43

7β-(α-Aminophenylacetamido)-6αH-8-oxo-4-thia-1-azabicyclo[4.2.0]oct-2-ene-2-carboxylic acid Benzhydryl bromopyruvate (500 mg) was dissolved in benzene (8 ml) and tetrahydrofuran (1 ml), cooled to 10° C and treated with a solution of diphenyldiazomethane (286 mg) in benzene (10 ml). The solution is stirred until colorless and then evaporated to dryness. The residue is dissolved in methylene chloride (5 ml) and cooled to 0° C and then cis-3-(α-t-butoxycarbonylaminophenylacetamido)-4-oxo-2-mercaptomethylazetidine (465 mg) is added. The reaction is stirred for one hour and evaporated to dryness to give a residue which dissoled in ethyl acetate-water. The ethyl acetate phase is washed with 1% HCl, NaHCO$_3$ solution and NaCl solution. The dried organic phase is evaporated to give benzhydryl 7-(α-t-butoxycarbonylaminophenylacetamido)-2-hydroxy-8-oxo-4-thia-1-azabicyclo[4.2.0]octane-2-carboxylate.

To a solution of the above product (200 mg) in ethyl acetate (4 ml) is added pyridine (150 μl). The solution is cooled to −10° C, stirred one hour with thionyl chloride (50 μl), diluted with water, acidified and extracted with ethyl acetate. The extracts are washed with 5% NaHCO$_3$ and NaCl solution, dried and evaporated. The residue is chromatographed over silica gel with 5:1 benzene-ethyl acetate as eluant to give the blocked derivative of the title product (50 mg).

The blocking groups are removed by stirring a solution of the above product (118 mg) in methylene chloride (10 ml), anisole (0.2 ml) and trifluoroacetic acid (2.0 ml) for 45 minutes at 0° C under argon. The reaction is allowed to warm to room temperature and then is evaporated to dryness under high vacuum. The trifluoroacetate salt of the title compound is triturated with ether and reprecipitated from methanol-ether.

EXAMPLE 44

7β-(α-Amino-p-hydroxypheylacetamido)-6αH-8-oxo-4-thia-1-azabicyclo[4.2.0]oct-2-ene-2-carboxylic acid To a solution of 265 mg (1 mmol) of N-t-butoxycarbonyl-p-hydroxyphenylglycine in dry tetrahydrofuran (10 ml) is added triethylamine (0.14 ml). After cooling to −10°, isobutyl chloroformate (1 mmol) in 2 ml of tetrahydrofuran is added dropwise and the reaction is stirred 20 minutes. A mixture of 270 mg (1 mmol) of cis-3-amino-4-oxo-2-azetidinemethyl tosylate and 0.14 ml of triethylamine in 50% aqueous tetrahydrofuran (5 ml) is cooled to −10° and added to the reaction solution. The resulting solution is stirred one hour at low temperature and then allowed to warm to room temperature. The organic solvent is removed and the aqueous residue is diluted with water and extracted with ethyl acette. The aqueous solution is layered with ethyl acetate, cooled and acidified. Phases are separated and the aqueous layer is extracted with ethyl acetate. The dried organic layers are evaporated to give the cis-3-(α-t-butoxycarbonylamino-p-hydroxyphenylacetamido)-4-oxo-2-azetidinylmethyl tosylate.

The above tosylate is reacted with NaI followed by p-methoxybenzyl mercaptan according to the procedure of Example 20 to give the p-methoxybenzylthio derivative which is cleaved by the procedure of Example 24 to give cis-3-(α-t-butoxycarbonylamino-p-hydroxypenylacetamido-4-oxo-2-mercaptomethylazetidine.

The above product is reacted with benzhydrylbromopyruvate according to the procedure of Example 43 and the subsequent reaction sequence disclosed therein is continued to give the title product.

EXAMPLE 45

7β-(2-Thienylacetamido-6αH-8-oxo-4-thia-1-azabicyclo-[4.2.0]oct-2-ene-2-carboxylic acid The dry ethyl acetate solution from Example 29 of trichloroethyl 7β-amino-6αH-8-oxo-4-thia-1-azabicyclo-[4.2.0]oct-2-ene-2-carboxylate which is obtained from 0.012 g of the t-butoxycarbonyl derivative is treated with 0.2 ml 2-thienylacetyl chloride and 0.2 ml of triethylamine. The reaction is stirred 2 hours at room temperature and then diluted with NaHCO$_3$ solution. The organic layer is separated, washed with 3N HCl, dried, and evaporated to give the 7-thienylacetamido derivative.

The above ester is treated with zinc dust and acetic acid according to the procedure in Example 42 to give the title product.

EXAMPLE 46

7β-Phenoxyacetamido-6αH-8-oxo-4-thia-1-azabicyclo[4.2.0]oct-2-ene-2-carboxylic acid The dry ethyl acetate solution of trichloroethyl 7β-amino-6αH-8-oxo-4-thia-1-azabicyclo[4.2.0]oct-2-ene-2-carboxylate from Example 29 is cooled to 0° and treated with one equivalent each of phenoxyacetyl chloride and triethylamine. After stirring 1 hours, the mixture is washed with dilute Hcl and brine. lThe organic phase is dried and evaporated to give trichloroethyl ester of the title product.

The trichloroethyl ester was treated with zinc dust and acetic acid by the procedure given in Example 42 to give the title product.

EXAMPLE 47

7β-Methylsulfonylacetamido-6αH-8-oxo-4-thia-1-azabicyclo-[4.2.0]oct-2-ene-2-carboxylic acid A solution of 200 mg (1 mmol) of trichloroethyl 7β-amino-6αH-8-oxo-4-thia-1-azabicyclo[4.2.0]oct-2-ene-2-carboxylate and 0.14 ml triethylamine in 10 ml of dimethylformamide is stirred with 236 mg (1 mmol) of the N-hydroxysuccinimide ester of methylsulfonylacetic acid for two hours at room temperature. The reaction is poured into ice water and the resultant solution is extracted with ethyl acetate. The aqueous phase is acidified to pH 2 and extracted with ethyl acetate. The dried extracts are evaporated to give the ester which is deblocked as in Example 42 to give the title product.

EXAMPLE 48

When trichloroethyl 7β-amino-6αH-8-oxo-4-thia-1-azabicyclo[4.2.0]oct-2-ene-2-carboxylic acid is acylated with one of the following carboxylic acids:

α-formyloxyphenylacetic acid
trifluoromethylmercaptoacetic acid
methylmercaptoacetic acid
2,2,2-trifluoroethylsulfinylacetic acid
cyanoacetic acid
cyanomethylmercaptoacetic acid
cyanomethylsulfinylacetic acid
cyanomethylsulfonylacetic acid
α-carboxy-2-thienylacetic acid
α-carboxy-3-thienylacetic acid
α-sulphophenylacetic acid
3-thienylacetic acid
1-tetrazoylacetic acid using the acid or an activated derivative thereof, all of which are known in the art, and which have any sensitive or interfering group suitably protected, according to known acylation procedures such as those set forth in Examples 43, 44, 45 or 47 followed by removal of all protecting groups by standard methods, gives the corresponding 7β-acylamino-6αH-8-oxo-4-thia-1-azabicyclo[4.2.0]oct-2-ene-2-carboxylic acid.

EXAMPLE 49

When α-(N-t-butoxycarbonylamino)-4-hydroxy-3-fluorophenylacetic acid or α-(N-t-butoxycarbonylamino)-4-(t-butoxycarbonylmethylamino)-phenylacetic acid is substituted for N-t-butoxycarbonyl-p-hydroxyphenylglycine in Example 44, the following compounds are obtained:

7β-(α-amino-4-hydroxy-3-fluorophenylacetamido)-6αH-8-oxo-4-thia-1-azabicyclo[4.2.0]oct-2-ene-2-carboxylic acid 7β-(α-amino-4-carboxymethylamino-phenylacetamido)-6αH-8-oxo-4-thia-1-azabicyclo[4.2.0]oct-2-ene-2-carboxylic acid.

EXAMPLE 50

7β-(α-Carboxyphenylacetamido)-6αH-8-oxo-4-thia-1-azabicyclo[4.2.0]oct-2-ene-2-carboxylic acid Equimolar quantities of the N-hydroxysuccinimidylester of α-t-butoxycarbonylphenylacetic acid, cis-3-amino-4-oxo-2-azetidinemethyl tosylate and triethylamine are stirred together in dimethylformamide for two hours at room temperature. The reaction is poured into ice water and the aqueous solution is washed with ethyl acetate, acidified to pH 2 and extracted with ethyl acetate. The dried extracts are evaporated to give the cis-3-(α-t-butoxycarbonylphenylacetamido)-4-oxo-2-azetidinylmethyl tosylate.

When the above tosylate is substituted for the tosylate in Example 44 and the reaction sequence disclosed therein is continued, the title product is obtained.

EXAMPLE 51

When 7β-amino-6αH-3-methyl-8-oxo-4-thia-1-azabicyclo[4.2.0]oct-2-ene-2-carboxylic acid is acylated with 2-thienylacetic acid, phenoxyacetic acid, methylsulfonylacetic acid, α-formyloxyphenylacetic acid, trifluoromethylmercaptoacetic acid, 2,2,2-trifluoroethylsulfinylacetic acid, cyanoacetic acid, cyanomethylmercaptoacetic acid, cyanomethylsulfinylacetic acid, cyanomethylsulfonylacetic acid, α-carboxy-2-thienylacetic acid, α-carboxy-3-thienylacetic acid, α-sulphophenylacetic acid, 3-thienylacetic acid, 1-tetrazolylacetic acid, α-aminophenylacetic acid, α-amino-p-hydroxyphenylacetic acid, α-amino-4-hydroxy-3-fluorophenylacetic acid, α-amino-p-carboxymethylaminophenylacetic acid, or α-carboxyphenylacetic acid, using the acid itself or an activated derivative thereof all of which are known in the art and which have any sensitive or interferring groups suitably protected, according to known acylation procedures such as those set forth in Examples 43, 44, 45 or 47 followed by removal of all protecting groups by standard methods, the corresponding 7β-acylamino-6αH-3-methyl-8-oxo-4-thia-1-azabicyclo[4.2.0]oct-2-ene-2-carboxylic acid is obtained.

EXAMPLE 52

When 7β-amino-6αH-3-acetoxymethyl-8-oxo-4-thia-1-azabicyclo[4.2.0]oct-2-ene-2-carboxylic acid is acylated with 2-thienylacetic acid, phenoxyacetic acid, methylsulfonylacetic acid, α-formyloxyphenylacetic acid, trifluoromethylmercaptoacetic acid, 2,2,2-trifluoroethylsulfinylacetic acid, cyanoacetic acid, cyanomethylmercaptoacetic acid, cyanomethylsulfinylacetic acid, cyanomethylsulfonylacetic acid, α-carboxy-2-thienylacetic acid, α-carboxy-3-thienylacetic acid, α-sulphophenylacetic acid, 3-thienylacetic acid, 1-tetrazolylacetic acid, α-aminophenylacetic acid, α-amino-p-hydroxyphenylacetic acid, α-amino-4-hydroxy-3-fluorophenylacetic acid, α-amino-p-carboxymethylaminophenylacetic acid, or α-carboxyphenylacetic acid, using the acid itself or an activated derivative thereof all of which are known in the art and which have any sensitive or interfering groups suitably protected, according to known acylation procedures such as those set forth in Examples 43, 44, 45 or 47 followed by removal of all protecting groups by standard methods, the corresponding 7β-acylamino-6αH-3-acetoxymethyl-8-oxo-4-thia-1-azabicyclo[4.2.0]oct-2-ene-2-carboxylic acid is obtained.

We claim:

1. A compound of the formula

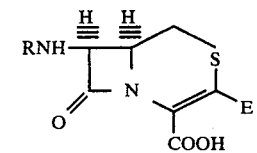

where

R is XCHCO, Y—CH$_2$CO or Z—S(O)$_n$CH$_2$CO;
    |
    A'

X is thienyl; cyclohexyl, cyclohexenyl, cyclohexdienyl, phenyl, or phenyl substituted with one or two substituents selected from the group consisting of lower alkyl, lower alkoxy, hydroxy, hydroxymethyl, halo, nitro, amino, aminomethyl, mercapto, lower alkylthio, trifluoromethyl, ureido, formamido and carboxymethylamino;

A' is amino, hydroxy, formyloxy, carboxyl or sulfonic acid;

Y is cyano, azido, phenyl, thienyl, furyl, thiazoyl, isothiazolyl, oxadiazolyl, thiadiazolyl, triazolyl, tetrazolyl, sydnone, pyridyl, or pyrimidyl, each heterocyclic ring being unsubstituted or substituted with one or two substituents selected from the group consisting of lower alkyl, lower alkoxy, halo, nitro, hydroxy, amino and phenyl;

Z is phenyl, pyridyl, lower alkyl, trifluoromethyl, trifluoroethyl or cyanomethyl;

$n$ is 0, 1, or 2; and

E is hydrogen, methyl, bromomethyl, or lower alkanoyloxymethyl, or a pharmaceutical acceptable salt thereof.

2. A compound as claimed in claim 1 where R is

and E is hydrogen, methyl, bromomethyl or acetoxymethyl.

3. A compound as claimed in claim 2 where X is thienyl, phenyl, 4-hydroxyphenyl, 4-hydroxy-3-fluorophenyl, or 4-carboxymethylaminophenyl.

4. A compound as claimed in claim 3 where A' is amino or hydroxy.

5. A compound as claimed in claim 4 being the compound 7β-(α-aminophenylacetamido)-6αH-8-oxo-4-thia-1-azabicyclo[4.2.0]oct-2-ene-2-carboxylic acid.

6. A compound as claimed in claim 4 being the compound 7β-mandelamido-6α-8-oxo-4-thia-1-azabicyclo[4.2.0]oct-2-ene-2-carboxylic acid.

7. A compound as claimed in claim 4 being the compound 7β-(α-amino-4-hydroxyphenylacetamido)-6αH-8-oxo-4-thia-1-azabicyclo[4.2.0]oct-2-ene-2-carboxylic acid.

8. A compound as claimed in claim 4 being the compound 7β-(α-aminophenylacetamido)-6αH-3-methyl-8-oxo-4-thia-1-azabicyclo[4.2.0]oct-2-ene-2-carboxylic acid.

9. A compound as claimed in claim 4 being the compound 7β-(α-amino-4-hydroxyphenylacetamido)-6αH-3-methyl-8-oxo-4-thia-1-azabicyclo[4.2.0]oct-2-ene-2-carboxylic acid.

10. A compound as claimed in claim 4 being the compound 7β-(α-aminophenylacetamido)-6αH-3-acetoxymethyl-8-oxo-4-thia-1-azabicyclo[4.2.0]oct-2-ene-2-carboxylic acid.

11. A compound as claimed in claim 4 being the compound 7β-mandelamido-6αH-3-acetoxymethyl-8-oxo-4-thia-1-azabicyclo[4.2.0]oct-2-ene-2-carboxylic acid.

12. A compound as claimed in claim 3 being the compound 7β-(α-carboxy-3-thienylacetamido)-6αH-8-oxo-4-thia-1-azabicyclo[4.2.0]oct-2-ene-2-carboxylic acid.

13. A compound as claimed in claim 1 where R is Y—CH$_2$CO and E is hydrogen, methyl, bromomethyl or acetoxymethyl.

14. A compound as claimed in claim 13 where Y is cyano, azido, phenoxy, thienyl, tetrazolyl or sydnone.

15. A compound as claimed in claim 14 being the compound 7β-phenoxyacetamido-6αH-8-oxo-4-thia-1-azabicyclo[4.2.0]oct-2-ene-2-carboxylic acid.

16. A compound as claimed in claim 14 being the compound 7β-cyanoacetamido-6αH-8-oxo-4-thia-1-azabicyclo[4.2.0]oct-2-ene-2-carboxylic acid.

17. A compound as claimed in claim 14 being the compound 7β-(1-tetrazolylacetamido)-6αH-8-oxo-4-thia-1-azabicyclo[4.2.0]oct-2-ene-2-carboxylic acid.

18. A compound as claimed in claim 14 being the compound 7β-(3-sydnoneacetamido)-6αH-8-oxo-4-thia-1-azabicyclo[4.2.0]oct-2-ene-2-carboxylic acid.

19. A compound as claimed in claim 14 being the compound 7β-(2-thienylacetamido)-6αH-8-oxo-4-thia-1-azabicyclo[4.2.0]oct-2-ene-2-carboxylic acid.

20. A compound as claimed in claim 14 being the compound 7β-(2-thienylacetamido)-6αH-3-acetoxymethyl-8-oxo--thia-1-azabicyclo[4.2.0] oct-2-ene-2-carboxylic acid.

21. A compound as claimed in claim 14 being the compound 7β-phenoxyacetamido-6αH-3-bromomethyl-8-oxo-4-thia-1-azabicyclo[4.2.0]oct-2-ene-4-carboxylic acid.

22. A compound as claimed in claim 14 being the compound 7β-phenoxyacetamido-6αH-3-acetoxymethyl-8-oxo-4-thia-1-azabicyclo[4.2.0]oct-2-ene-4-carboxylic acid.

23. A compound as claimed in claim 1 where R is Z—S(O)$_n$CH$_2$CO and E is hydrogen, methyl, bromomethyl or acetoxymethyl.

24. A compound as claimed in claim 23 where Z is phenyl.

25. A compound as claimed in claim 23 where Z is pyridyl and n is 0.

26. A compound as claimed in claim 25 being the compound 7β-(4-pyridylthioacetamido)-6αH-8-oxo-4-thia-1-azabicyclo[4.2.0]oct-2-ene-2-carboxylic acid.

27. A compound as claimed in claim 23 where Z is methyl.

28. A compound as claimed in claim 27 being the compound 7β-methylmercaptoacetamido-6αH-8-oxo-4-thia-1-azabicyclo[4.2.0]0ct-2-ene-2-carboxylic acid.

29. A compound as claimed in claim 27 being the compound 7β-methylsulfonylacetamido-6αH-8-oxo-4-thia-1-azabicyclo[4.2.0]oct-2-ene-2-carboxylic acid.

30. A compound as claimed in claim 23 where Z is trifluoromethyl.

31. A compound as claimed in claim 30 being the compound 7β-trifluoromethylmercaptoacetamido-6αH-8-oxo-4-thia-1-azabicyclo[4.2.0]oct-2-ene-2-carboxylic acid.

32. A compound as claimed in claim 23 where Z is trifluoroethyl.

33. A compound as claimed in claim 32 being the compound 7β-trifluoroethylsulfinylacetamido-6αH-8-oxo-4-thia-1-azabicyclo[4.2.0]oct-2-ene-2-carboxylic acid.

34. A compound as claimed in claim 23 where Z is cyanomethyl.

35. A compound as claimed in claim 34 being the compound 7β-cyanomethylmercaptoacetamido-6αH-8-oxo-4-thia-1-azabicyclo[4.2.0]oct-2-ene-2-carboxylic acid.

36. A compound as claimed in claim 34 being the compound 7β-cyanomethylsulfinylacetamido-6αH-8-oxo-4-thia-1-azabicyclo[4.2.0]oct-2-ene-2-carboxylic acid.

37. A compound as claimed in claim 34 being the compound 7β-cyanomethylsulfonylacetamido-6αH-8-oxo-4-thia-1-azabicyclo[4.2.0]oct-2-ene-2-carboxylic acid.

38. A compound of the formula

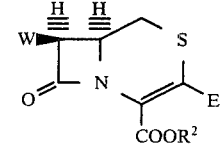

where:
E is hydrogen, methyl, bromomethyl or lower alkanoyloxymethyl;
W is (R')$_2$N;
R$^2$ is hydrogen or a removable carboxyl protecting group; and
each R' is hydrogen or a monovalent removable amino protecting group or, when both R' groups are taken together, a divalent removable amino protecting group.

39. A compound as claimed in claim 38 where R$^2$ is hydrogen, 2,2,2-trichloroethyl, C$_4$-C$_6$-tert-alkyl, C$_5$-C$_7$-tert-alkenyl, C$_5$ to C$_7$-tert-alkynyl, C$_1$-C$_6$ alkanoylmethyl, N-phthalimidomethyl, benzoylmethyl, naphthoylmethyl, furoylmethyl, thienoylmethyl, nitrobenzoylmethyl, halobenzoylmethyl, methylbenzoylmethyl, methanesulfonylbenzoylmethyl, phenylbenzoylmethyl, benzyl, nitrobenzyl, methoxybenzyl, benzhydryl, trityl, trimethylsilyl or triethylsilyl; R' is hydrogen, trityl, t-butoxycarbonyl, trichloroethoxycarbonyl, benzyloxycarbonyl, methoxybenzylcarbonyl, isobornyloxycarbonyl, or methyl acetoacetate adduct or (R')$_2$N is 4,5-diphenyl-2-oxo-4-oxazolin-3-yl or phthalimido and E is hydrogen, methyl, bromomethyl or acetoxymethyl.

40. A compound as claimed in claim 39 where $R^2$ is hydrogen, 2,2,2-trichloroethyl, t-butyl, benzyl, benzhydryl, benzyloxymethyl, p-nitrophenyl, p-methoxyphenyl, p-nitrobenzyl, or p-methoxybenzyl.

41. A compound as claimed in claim 40 where E is hydrogen.

42. A compound as claimed in claim 40 where E is methyl.

43. A compound as claimed in claim 40 where E is acetoxymethyl.

44. A compound as claimed in claim 40 where E is bromomethyl.

45. A compound as claimed in claim 44 being the compound t-butyl, 7β-t-butoxycarbonylamino-6αH-3-bromomethyl-8-oxo-4-thia-1-azabicyclo[4.2.0]oct-2-ene-2-carboxylate.

46. A compound as claimed in claim 41 where R' is hydrogen.

47. A compound as claimed in claim 42 where R' is hydrogen.

48. A compound as claimed in claim 43 where R' is hydrogen.

49. A compound as claimed in claim 41 being the compound trichloroethyl 7β-t-butoxycarbonylamino-6αH-8-oxo-4-thia-1-azabicyclo[4.2.0]oct-2-ene-2-carboxylate.

50. A compound as claimed in claim 46 being the compund trichloroethyl 7β-amino-6αH-8-oxo-4-thia-1-azabicyclo[4.2.0]oct-2-ene-2-carboxylate.

51. A compound as claimed in claim 46 being the compound 7β-amino-6αH-8-oxo-4-thia-1-azabicyclo[4.2.0]oct-2-ene-2-carboxylic acid.

52. A compound as claimed in claim 41 being the compound benzhydryl 7β-t-butoxycarbonylamino-6αH-8-oxo-4-thia-1-azabicyclo[4.2.0]oct-2-ene-2-carboxylate.

53. A compound as claimed in claim 41 being the compound t-butyl 7β-t-butoxycarbonylamino-6αH-8-oxo-4-thia-1-azabicyclo[4.2.0]oct-2-ene-2-carboxylate.

54. A compound as claimed in claim 42 being the compound benzhydryl 7β-t-butoxycarbonylamino-6αH-3-methyl-8-oxo-4-thia-1-azabicyclo[4.2.0]oct-2-ene-2-carboxylate.

55. A compound as claimed in claim 42 being the compound t-butyl 7β-t-butoxycarbonylamino-6αH-3-methyl-8-oxo-4-thia-1-azabicyclo[4.2.0]oct-2-ene-2-carboxylate.

56. A compound as claimed in claim 47 being the compound 7β-amino-6αH-3-methyl-8-oxo-4-thia-1-azabicyclo-[4.2.0]oct-2-ene-2-carboxylic acid.

57. A compound as claimed in claim 43 being the compound t-butyl 7β-t-butoxycarbonylamino-6αH-3-acetoxymethyl-8-oxo-4-thia-1-azabicyclo[4.2.0]oct-2-ene-2-carboxylate.

58. A compound as claimed in claim 48 being the compound 7β-amino-6αH-3-acetoxymethyl-8-oxo-4-thia-1-aza-bicyclo[4.2.0]oct-2-ene-2-carboxylic acid.

\* \* \* \* \*

UNITED STATES PATENT AND TRADEMARK OFFICE
CERTIFICATE OF CORRECTION

PATENT NO. : 4,103,086

DATED : July 25, 1978

INVENTOR(S) : John G. Gleason, Kenneth G. Holden and William F. Huffman

It is certified that error appears in the above–identified patent and that said Letters Patent are hereby corrected as shown below:

Column 29, line 2, change --6α-- to "6αH"

Column 29, line 49, change --oxo---thia-- to "oxo-4-thia"

Column 30, line 5, change --Oct-- to "oct"

Signed and Sealed this

Sixth Day of February 1979

[SEAL]

Attest:

RUTH C. MASON
Attesting Officer

DONALD W. BANNER
Commissioner of Patents and Trademarks